United States Patent [19]

Fotiu et al.

[11] 3,978,207

[45] Aug. 31, 1976

[54] PRESSED POWDER COSMETIC COMPOSITION

[75] Inventors: Eustace Fotiu, Mahwah; Monroe Lanzet, Pine Brook, both of N.J.; Julio Russ, East Meadow, N.Y.

[73] Assignee: Revlon, Inc., New York, N.Y.

[22] Filed: Mar. 21, 1975

[21] Appl. No.: 560,642

Related U.S. Application Data

[63] Continuation-in-part of Ser. No. 317,177, Dec. 21, 1972, abandoned.

[52] U.S. Cl. .................................................. 424/63
[51] Int. Cl.² ................. A61K 7/021; A61K 7/031; A61K 7/032
[58] Field of Search ...................... 424/63; 317/177

[56] References Cited
UNITED STATES PATENTS

| | | | |
|---|---|---|---|
| 2,101,843 | 12/1937 | Factor et al. | 424/63 |
| 2,278,970 | 4/1942 | Atwood | 106/291 X |
| 2,979,108 | 4/1961 | Thompson | 106/291 X |
| 3,296,078 | 1/1967 | Kaye et al. | 424/63 |
| 3,471,611 | 10/1969 | Scott et al. | 424/63 X |
| 3,597,250 | 8/1971 | Rands, Jr. et al. | 106/291 |

FOREIGN PATENTS OR APPLICATIONS

| | | | |
|---|---|---|---|
| 58,357 | 10/1967 | Germany | 424/63 |
| 2,599 | 1/1971 | Japan | 424/63 |
| 501,426 | 5/1937 | United Kingdom | 424/63 |
| 1,128,312 | 9/1968 | United Kingdom | 424/63 |

*Primary Examiner*—Dale R. Ore
*Attorney, Agent, or Firm*—Leon E. Tenenbaum

[57] ABSTRACT

Compositions of nacreous materials suitable for compression into pressed cakes for use in cosmetics are obtained by mixing 3 to 9 parts of a nacreous material, such as mica, with 1 to 5 parts of a binder oil such as a liquid lanolin absorption base.

8 Claims, No Drawings

PRESSED POWDER COSMETIC COMPOSITION

This application is a continuation-in-part of patent application Ser. No. 317,177, filed Dec. 21, 1972, now abandoned.

This invention relates to cosmetic preparations. It particularly relates to pressed powder cosmetics having frosted pearl effects and to a process for their preparation.

Pressed cakes containing nacreous materials such as, for example, mica, bismuth oxychloride, or coated mica such as, for example, titanated mica or mica coated with bismuth oxychloride, have been widely used in the cosmetic field to convey a pearlized effect. However, with present techniques, pressed cakes containing more than 30–35% by weight of mica cannot be prepared. This is apparently due to poor compaction because of the flat platelet structure of the mica particles. While other ingredients giving a pearl essence effect, such as, for example, up to 50% by weight of bismuth oxychloride, may be added to mica to improve lustre and aid in compaction, the addition of such ingredients does not solve the problem with regard to poor compaction of compositions containing higher concentrations of mica. Hereinafter in the description, unless otherwise noted, the term "mica" will refer to mica per se as well as coated micas.

While cakes containing about 30–35% of pressed mica have been used, cosmetics prepared from such cakes have poor reflectivity on the skin. Better reflectivity can only be obtained with higher concentrations of the mica. Binders, such as oils, are used in these cakes, but the use of higher concentrations of oils such as isopropyl myristate, mineral oil and liquid lanolin esters produce surface glazing, a common defect in such preparations, which prevents the full utilization of the entire pressed cake. Furthermore, the pressed cakes of the present art manifest poor skin adhesion and poor application properties, that result in poor wear properties of the cosmetic preparations.

Attempts to prepare stable pressed cakes containing higher concentrations of mica by using higher pressures of the order of 4,500 psig have not been successful in providing stable pressed cakes having desirable mechanical and application properties.

It is, accordingly, an object of the present invention to provide compositions containing high concentrations of nacreous materials, such as mica, alone or with bismuth oxychloride, which can be compressed with good compaction.

It is another object of the present invention to provide such compositions which are resistant to glazing.

It is still another object of the present invention to provide a process for obtaining such compositions.

It is a further object of the present invention to provide such compositions having excellent skin adhesion, good application characteristics and superior lasting qualities on the skin.

It is still a further object of the present invention to provide such compositions which can be compressed into cakes at lower pressures.

Other objects will become apparent in the description which follows.

In accordance with the present invention we have found that the addition to particles of mica of a liquid binder, described below, will provide compositions containing high concentrations of mica and the like, which may be readily compressed to give stable pressed cakes having desirable properties. In practice we use from 1 to 5 parts by weight of the liquid binder to 3 to 9 parts by weight of the mica or other nacreous materials.

The liquid binder is a liquid lanolin absorption base. Lanolin absorption bases are mixtures of lanolin and/or lanolin alcohols with petrolatum and/or mineral oil. These bases may also contain emulsifiers to improve stability. Examples of such lanolin absorption bases are given in Balsam and Sagarin, "Cosmetics" — Science and Technology, 2nd Edition, 1972, Wiley - Interscience, New York, Vol. I, page 52. These bases are diluted with a sufficient amount oil to give the desired liquidity. The liquid lanolin absorption bases, thus prepared, contain from about 80 to 90% by weight of oil.

Hereinafter, unless otherwise noted, the term "oil" will refer to mineral oil, liquid long chain alcohols (e.g. oleyl alcohol), liquid esters of long chain fatty acids (e.g. isopropyl myristate), and liquid esters of long chain alcohols (e.g. hexadecyl adipate).

Other suitable liquid binders are liquid lanolin absorption bases such as Amerchol L-101, a base containing from about 3.8 to 8% of sterols, principally cholesterol, dihydrocholesterol lanosterol and 7-hydroxycholesterol and from about 3–5% of high molecular weight fatty alcohols, in a hydrocarbon solvent, supplied by the Amerchol Chemical Co. Division of CPC International.

Other liquid binders that are suitable for use in the practice of the present invention are oil solutions of waxes or lanolin alcohols. Although all waxes which are soluble in the oil are suitable, we prefer to use a microcrystalline wax such as ceresin. A 10% by weight solution of ceresin or lanolin alcohols in mineral oil (viscosity 70 Saybolt) has been found very useful in the practice of the present invention.

In addition, if desired, colorants (e.g. inorganic pigments and certified organic colors) may be added prior to pressing to provide desired color effects, and perfumes to provide desired aromas. Also, if desired, water, antioxidants and preservatives may be added.

The pressed compositions are formulated to contain from about 30 to 90% by weight of the desired nacreous material.

In preparing the compositions of the present invention we either disperse the liquid binder on the mica or blend the mica and the binder. The mixture of the mica and binder is then formed into a uniform mass which is fed into pans and then compressed at pressures of about 2,000 to 6,000 psig.

Colorants, perfumes, preservatives, antioxidants, and water may be added if desired. However, in adding colorants, we have found that it is of importance to uniformly blend the colorant uniformly into the liquid binder prior to mixing the binder with the nacreous substance. By following this procedure we obtain an intimate and exceptionally uniform coating of the colorant on the nacreous material.

The invention will be more fully understood from the examples which follow. These examples are given by way of illustration and are not to be considered as limiting.

EXAMPLE 1

9 parts by weight of a mineral oil solution of microcrystalline wax prepared from a mineral oil having a visiosity 70 Saybolt was dispersed on the surface of a blend of 85 parts by weight of mica particles together with 5 parts by weight of chromic oxide color in a ribbon or planetary mixer by spraying. The dispersion operation was also carried out in a Patterson Kelley Twin Shell Blendor equipped with a liquid feed and intensifier bar. An alternate method to assure thorough dispersion when using a ribbon blendor was to pass the mass once through a Mikro Pulverizer or similar hammer mill fitted with a jump gap reverse screen to minimize destruction of the crystal platelets. The oil coated mass remained powdery and was then fed into pans for pressing at pressures at about 4,000 psig.

The pressed cakes so produced have good adhesion to the pan and may be applied to the skin using either the finger or sponge or brush applicators. Dusting from the pan is virtually absent and the product exhibits excellent skin adhesion and even applicator characteristics. Furthermore, glazing of the cake is absent even when application is by finger. The high mica content effectively prevents this glazing phenomenon.

EXAMPLE 2

35 parts by weight of ferric oxide and 65 parts by weight of a mineral oil solution containing 10% by weight of lanolin alcohols were preblended in a change can mixer or similar equipment. When thoroughly preblended, the mixture was passed through a 3 roll ointment mill, colloid mill or similar equipment until a smooth paste was achieved with fine uniform particle size. 20 parts by weight of this color grind was then combined with 70 parts by weight of mica, together with a preservative and water totalling 10 parts by weight. The powdery, essentially free flowing mass is uniformly blended and then in accordance with the procedure described in Example 1 pressed into pans.

This process is suitable for production of either shiny lustrous or matte pressed cakes for use as skin pigments. These preparations may be used as eye shadow, cheek color, facial make-up or lip color.

EXAMPLE 3

|  | % by Wt. |
|---|---|
| Titanated Mica Interference Color | 78 |
| Lanolin Absorption Base | 16 |
| Water | 6 |

The composition as shown above was combined as described in Example 1 and pressed into pans. This non-glazing eye shadow composition may be applied to the lids by finger or use of a brush or sponge applicator. Additionally, it may be applied with a water wet applicator for other skin coloration effects without destruction of the cake or glazing, and when air dried can be reused by either wet or dry techniques. The cake so prepared is sufficiently hydrophilic to accept the water and form a temporary emulsion during application.

When applied "dry" and then buffed lightly by finger, brush or sponge, the mica film laminates (i.e. orients parallel to the skin) forming an even more tenacious film with exceptionally good wearing characteristics. When coated mica (e.g. titanium coated mica) is used in the composition, the skin lustre of the film is considerably enhanced while adhesion to the skin and evenness remain virtually unaffected.

EXAMPLE 4

A cheek or lip color cake was prepared using the formula below:

|  | % by Wt. |
|---|---|
| Titanium Coated Mica | 59.3 |
| Certified Organic Color Lakes | 7.7 |
| Lanolin Absorption Base | 32.0 |
| Preservatives, anti-oxidants & perfume | 1.0 |

The desired color blend was ground into the binder oil as described in Example 2 and then combined to form a uniformly coated powdery composition by combination with the remaining ingredients as described in Example 2, and then pressed into pans.

The pressed cakes so produced can be easily applied to the cheeks or lips to provide a oily, lustrous adherent color film with excellent wear properties and more lasting pearl affects that are manifest with conventional lipsticks and cream color preparations. The resultant product is further characterized by absence of "bleeding", "creasing" and other disadvantages of wax based cheek and lip colorants.

Additionally, no greasy film is sensed, and when used on the lips, transfer to skin, glasses and cigarettes is minimized as compared to conventional pearly lipsticks.

Following the procedures in the above examples, pressed cakes of other coated micas such as mica coated with bismuth oxychloride were similarly prepared. If desired, instead of using only one of these substances, combinations of 2 or more substances, such as, for example, mica per se and a coated mica may be used. Instead of using mica coated with bismuth oxychloride, the bismuth oxychloride may be added to the mica prior to formulation.

We claim:

1. A pressed powder cosmetic composition containing from about 30 to 90% by weight of a nacreous material selected from the group consisting of mica and a coated mica, said coated mica being selected from the group consisting of titanated mica and mica coated with bismuth oxychloride, comprising from about 3 to 9 parts by weight of said nacreous material and from about 1 to 5 parts by weight of a liquid binder selected from the group consisting of a liquid lanolin absorption base and an oil solution of a wax or a lanolin alcohol, wherein the oil is a mineral oil, a liquid long chain alcohol, a liquid ester of a long chain fatty acid, or a liquid ester of a long chain alcohol.

2. A composition according to claim 1 wherein the liquid binder is a 10% by weight solution of a microcrystalline wax or a lanolin alcohol in mineral oil having a viscosity of 70 Saybolt.

3. A composition according to claim 2 wherein the nacreous material is mica.

4. A composition according to claim 2 wherein the nacreous material is titanated mica.

5. A composition according to claim 2 wherein the nacreous material is mica coated with bismuth oxychloride.

6. A composition according to claim 1 which also contains a coloring material selected from the group consisting of an inorganic pigment and a certified organic color cake.

7. A composition according to claim 1 wherein the pressed cake contains in percent by weight

| | |
|---|---|
| titanated mica interference color | 78 |
| liquid lanolin absorption base | 16 |
| water | 6. |

8. A composition according to claim 1 wherein the pressed cake contains in percent by weight

| | |
|---|---|
| titanium coated mica | 59.3 |
| certified organic color lakes | 7.7 |
| liquid lanolin absorption base | 32.0 |
| preservatives, anti-oxidants and perfume | 1.0. |

* * * * *